(12) United States Patent
Mizutani et al.

(10) Patent No.: US 9,921,235 B2
(45) Date of Patent: Mar. 20, 2018

(54) AUTOMATIC ANALYZER AND SAMPLE DISPENSING METHOD FOR THE AUTOMATIC ANALYZER

(71) Applicant: Beckman Coulter, Inc., Brea, CA (US)

(72) Inventors: Takayuki Mizutani, Shizuoka (JP); Kiyotaka Kubota, Shizuoka (JP)

(73) Assignee: Beckman Coulter, Inc., Brea, CA (US)

( * ) Notice: Subject to any disclaimer, the term of this patent is extended or adjusted under 35 U.S.C. 154(b) by 118 days.

(21) Appl. No.: 14/680,970

(22) Filed: Apr. 7, 2015

(65) Prior Publication Data

US 2015/0226761 A1    Aug. 13, 2015

Related U.S. Application Data

(63) Continuation of application No. 13/132,053, filed as application No. PCT/JP2009/055514 on Mar. 19, 2009, now abandoned.

(30) Foreign Application Priority Data

Dec. 4, 2008  (JP) .................................. 2008-310028

(51) Int. Cl.
G01N 35/10       (2006.01)
G01N 35/02       (2006.01)
(Continued)

(52) U.S. Cl.
CPC ..... *G01N 35/1072* (2013.01); *G01N 33/5304* (2013.01); *G01N 35/0095* (2013.01);
(Continued)

(58) Field of Classification Search
CPC ............. G01N 35/0092; G01N 35/025; G01N 35/0439; G01N 35/0444; G01N 35/0453; G01N 35/0496; G01N 35/1065
See application file for complete search history.

(56) References Cited

U.S. PATENT DOCUMENTS

| 4,774,055 A | 9/1988 | Wakatake et al. |
| 5,411,065 A * | 5/1995 | Meador .................. B01L 3/505 141/1 |

(Continued)

FOREIGN PATENT DOCUMENTS

| CN | 1621846 A | 6/2005 |
| CN | 1790027 A | 6/2006 |

(Continued)

OTHER PUBLICATIONS

The International Search Report from PCT/JP2009/055514, dated Jun. 9, 2009, included English Translation, 2 pages.

(Continued)

*Primary Examiner* — Christopher Adam Hixson
(74) *Attorney, Agent, or Firm* — Kilpatrick Townsend & Stockton LLP

(57) ABSTRACT

An automatic analyzer capable of avoiding carry-over between samples, and a sample dispensing method, are provided. To that end, an automatic analyzer (1) for performing analysis of both assay menu with a high carry-over avoiding level and assay menu with a low carry-over avoiding level, includes: a first sample dispensing apparatus (6) loaded with a disposable tip (60*a*) for sample dispensing for assay menu with a high carry-over avoiding level, and for subdividing and dispensing a sample for assay menu with a low carry-over avoiding level; an aliquot container (9) for subdividing and containing a sample for assay menu with a low carry-over avoiding level, subdivided and dispensed by the first sample dispensing apparatus (6); and a second sample dispensing apparatus (5) loaded with a reusable probe (50), for sample dispensing for assay menu with a low carry-over avoiding level.

19 Claims, 9 Drawing Sheets

(51) Int. Cl.
    *G01N 33/53*     (2006.01)
    *G01N 35/00*     (2006.01)
    *G01N 35/04*     (2006.01)

(52) U.S. Cl.
    CPC ..... *G01N 35/00603* (2013.01); *G01N 35/025* (2013.01); *G01N 35/1004* (2013.01); *G01N 35/1011* (2013.01); *G01N 35/0098* (2013.01); *G01N 2035/00277* (2013.01); *G01N 2035/00326* (2013.01); *G01N 2035/0444* (2013.01); *G01N 2035/0472* (2013.01); *G01N 2035/103* (2013.01); *G01N 2035/1032* (2013.01); *Y10T 436/2575* (2015.01)

(56) References Cited

U.S. PATENT DOCUMENTS

| | | | |
|---|---|---|---|
| 5,501,984 A * | 3/1996 | Hofstetter | G01N 35/1065 422/63 |
| 5,587,129 A | 12/1996 | Kurosaki et al. | |
| 5,670,113 A * | 9/1997 | Akong | G01N 33/502 356/414 |
| 6,752,960 B1 * | 6/2004 | Matsubara | G01N 35/1004 422/552 |
| 2002/0031837 A1 | 3/2002 | Matsubara et al. | |

FOREIGN PATENT DOCUMENTS

| | | |
|---|---|---|
| JP | 08-094636 A | 4/1996 |
| JP | 08-278313 A | 10/1996 |
| JP | 2000-146987 A | 5/2000 |
| JP | 2005-156272 A | 6/2006 |
| JP | 2006-170735 A | 6/2006 |
| WO | 2008/050397 A1 | 2/2008 |

OTHER PUBLICATIONS

Chinese Office Action dated Mar. 18, 2013 for CN Patent Application No. 200980149041.4, 7 pages.

European Search Report dated Jan. 9, 2014 for EP Patent Application No. 09830227.6, 9 pages.

\* cited by examiner

AUTOMATIC ANALYZER AND SAMPLE DISPENSING METHOD FOR THE AUTOMATIC ANALYZER

CROSS-REFERENCE TO RELATED APPLICATION

This application is continuation of U.S. patent application Ser. No. 13/132,053 filed on May 31, 2011, which is a National Stage of International Application No. PCT/JP2009/055514, filed Mar. 19, 2009, which claims the benefit of priority to Japanese Application No. 2008-310028, filed Dec. 4, 2008, the disclosures of which are herein incorporated by reference.

TECHNICAL FIELD

The present invention relates to an automatic analyzer for performing analysis of assay menu with different carry-over avoiding levels, and a sample dispensing method used for the automatic analyzer.

BACKGROUND ART

In recent years, a multi-purpose apparatus or an integrated apparatus used for both a biochemical analysis and an immunological analysis, obtained by equipping a biochemical analyzer with modules handling various kinds of immunological assay menu; and a composite apparatus obtained by installing a biochemical analysis module and an immunological analysis module into an automatic analyzer, have been developed along with the trend of labor saving in testing rooms.

However, the immunological assay menu has an extremely large difference in numerical values between normal values and abnormal values. Even with a minute amount of carry-over between samples, which is not considered to be problematic in a biochemical assay menu, there is a possibility of causing a false positive judgment due to the carry-over. Thus, in order to prevent carry-over between samples in such a multi-purpose apparatus or an integrated apparatus for a biochemical analysis and an immunological analysis, an automatic analysis system is disclosed which performs an immunological analysis first and a biochemical analysis subsequently, and which inserts a dispensing probe in the interior of a sample to reduce the influence of carry-over when there is a necessity of performing a retest in immunological assay menu (e.g., see Patent Reference 1).

Further, an analysis method is disclosed in which a disposable nozzle tip is used for the dispensing of assay menu with a high carry-over avoiding level, a repeatedly used nozzle is used for the dispensing of assay menu with a low carry-over avoiding level, and the analysis of the assay menu with a low carry-over avoiding level is performed when it is judged that a retest is not necessary from an analysis result of the assay menu with a high carry-over level (e.g. see Patent References 2 and 3).

Patent Reference 1: Japanese Patent No. 3845301
Patent Reference 2: Japanese Patent No. 3380542
Patent Reference 3: Japanese Patent No. 4101466

DISCLOSURE OF THE INVENTION

Problems to be Solved by the Invention

In the automatic analysis described in Patent Reference 1, however, although it is possible to reduce the influence of carry-over compared to a case of dispensing from a sample liquid level, it is not possible to avoid the carry-over completely. Moreover, the sample dispensing is not simultaneously performed for an immunological analysis and a biochemical analysis.

Although the analysis method described in Patent Reference 2 or 3 is capable of avoiding carry-over, the analysis cannot be performed for assay menu with a low carry-over avoiding level until it is judged whether or not a retest is necessary for assay menu with a high carry-over avoiding level. Thus, the subject analysis method has a problem of significantly reducing processing capacity.

The present invention is intended to solve the problems described above. It is an object of the present invention to provide an automatic analyzer and a sample dispensing method, capable of avoiding carry-over between samples and significantly improving processing capacity.

Means for Solving the Problem

An automatic analyzer according to the present invention for performing analysis of both an assay menu with a high carry-over avoiding level and an assay menu with a low carry-over avoiding level includes: a first sample dispensing section for performing sample dispensing for an assay menu with a high carry-over avoiding level, and the subdividing and dispensing of a sample for an assay menu with a low carry-over avoiding level, by loading a disposable tip thereto; a housing section for subdividing and housing the sample for an assay menu with a low carry-over avoiding level, which is subdivided and dispensed by the first sample dispensing section; and a second sample dispensing section for performing the dispensing of the sample for an assay menu with a low carry-over avoiding level, by loading a reusable probe thereto, where the second sample dispensing section dispenses the sample from the housing section, thereby achieving the object described above.

In one embodiment, the automatic analyzer according to the present invention performs sample dispensing from a sample container for an assay menu with a high carry-over avoiding level by the first sample dispensing section, and sample dispensing from the housing section for an assay menu with a low carry-over avoiding level, in parallel with each other for the same sample.

In another embodiment, in the automatic analyzer according to the present invention, the housing section is provided at a position above loci of dispensing probes of the first sample dispensing section and the second sample dispensing section, and at which the loci intersect with each other.

In still other embodiment, the automatic analyzer according to the present invention further includes a conveying section for conveying the housing section to a position at which the sample is subdivided by the first sample dispensing section, and to a position at which the sample is dispensed by the second sample dispensing section.

In still other embodiment, in the automatic analyzer according to the present invention, the assay menu with a high carry-over avoiding level is an immunological assay menu or a genetical assay menu, and the assay menu with a low carry-over avoiding level is a biochemical assay menu.

In still other embodiment, in the automatic analyzer according to the present invention, the first sample dispensing section and the second sample dispensing section are respectively included in two arms that independently pivot, but have a common pivoting axis.

In still other embodiment, in the automatic analyzer according to the present invention, the housing section is an aliquot container.

In still other embodiment, in the automatic analyzer according to the present invention, the aliquot container is washed and reused every time a sample to be contained is changed.

In still other embodiment, in the automatic analyzer according to the present invention, the aliquot container is disposed and replaced with a new container every time a sample to be contained is changed.

In still other embodiment, the automatic analyzer according to the present invention further includes: a calculation section for calculating a sample amount required for analysis of an assay menu with a low carry-over avoiding level, for each sample; and a recording section for storing the sample amount calculated by the calculation section.

In still other embodiment, the automatic analyzer according to the present invention further includes a dispensation controlling section for the control of: the dispensing from the sample container using the first sample dispensing section loaded with a new disposable tip when a retest is conducted for an assay menu with a high carry-over avoiding level; and the subdividing of the sample from the sample container to the housing section, using the first sample dispensing section loaded with a new disposable tip, and subsequently the dispensing from the housing section using the second sample dispensing section, when a retest is conducted for an assay menu with a low carry-over avoiding level.

In still other embodiment, the automatic analyzer according to the present invention further includes a washing apparatus for washing the probe of the second sample dispensing section.

In still other embodiment, in the automatic analyzer according to the present invention, an analysis module for analyzing an as say menu with a high carry-over avoiding level, and an analysis module for analyzing an assay menu with a low carry-over avoiding level are provided as an independent unit.

In still other embodiment, in the automatic analyzer according to the present invention, an analysis module for analyzing an as say menu with a high carry-over avoiding level, and an analysis module for analyzing an assay menu with a low carry-over avoiding level are provided in one unit.

A sample dispensing method according to the present invention for an automatic analyzer for performing analysis of both an assay menu with a high carry-over avoiding level and an assay menu with a low carry-over avoiding level, includes: a subdividing and dispensing step for dispensing a sample required for analysis of an assay menu with a low carry-over avoiding level, from a sample container to a housing section, using a first sample dispensing section for an assay menu with a high carry-over avoiding level, which is loaded with a disposable tip; a first sample dispensing step, for the same sample, for dispensing a sample for an assay menu with a high carry-over avoiding level, from the sample container, using the first sample dispensing section; and a second sample dispensing step, for the same sample, for dispensing a sample for an assay menu with a low carry-over avoiding level, from the housing section, using a second sample dispensing section loaded with a reusable probe.

In an embodiment, in the sample dispensing method for an automatic analyzer according to the present invention, the first sample dispensing step and the second sample dispensing step are performed in parallel with each other for the same sample.

In another embodiment, in the sample dispensing method for an automatic analyzer according to the present invention, the assay menu with a high carry-over avoiding level is an immunological assay menu or a genetical assay menu, and the assay menu with a low carry-over avoiding level is a biochemical assay menu.

In still other embodiment, in the sample dispensing method for an automatic analyzer according to the present invention, the housing section is an aliquot container.

In still other embodiment, in the sample dispensing method for an automatic analyzer according to the present invention, the aliquot container is washed and used every time a sample to be contained is changed.

In still other embodiment, in the sample dispensing method for an automatic analyzer according to the present invention, the aliquot container is replaced with a new container every time a sample to be contained is changed.

In still other embodiment, the sample dispensing method for an automatic analyzer according to the present invention further includes: a calculation step for calculating a sample amount required for analysis of an assay menu with a low carry-over avoiding level, for each sample; and an extraction step for extracting the sample amount from a recording section for storing the sample amount calculated in the calculation step.

In still other embodiment, the sample dispensing method for an automatic analyzer according to the present invention further includes: performing the dispensing from the sample container using the first sample dispensing section loaded with a new disposable tip when a retest is conducted for an assay menu with a high carry-over avoiding level; and subdividing the sample from the sample container to the housing section, using the first sample dispensing section loaded with a new disposable tip, and subsequently dispensing the sample from the housing section using the second sample dispensing section, when a retest is conducted for an assay menu with a low carry-over avoiding level.

In still other embodiment, the sample dispensing method for an automatic analyzer according to the present invention further includes a tip replacing step for disposing and replacing the disposable tip of the first sample dispensing section after the first sample dispensing step.

In still other embodiment, in the sample dispensing method for an automatic analyzer according to the present invention, the second sample dispensing step includes a washing step for washing a probe of the second sample dispensing section using a washing apparatus every time the dispensing is completed for each assay menu.

In the present invention, it becomes possible to avoid carry-over in the retest of assay menu with a high carry-over avoiding level, and to improve processing capacity significantly without pausing (putting on hold) sample dispensing for assay menu with a low carry-over avoiding level and subsequent analysis.

Figure 1:
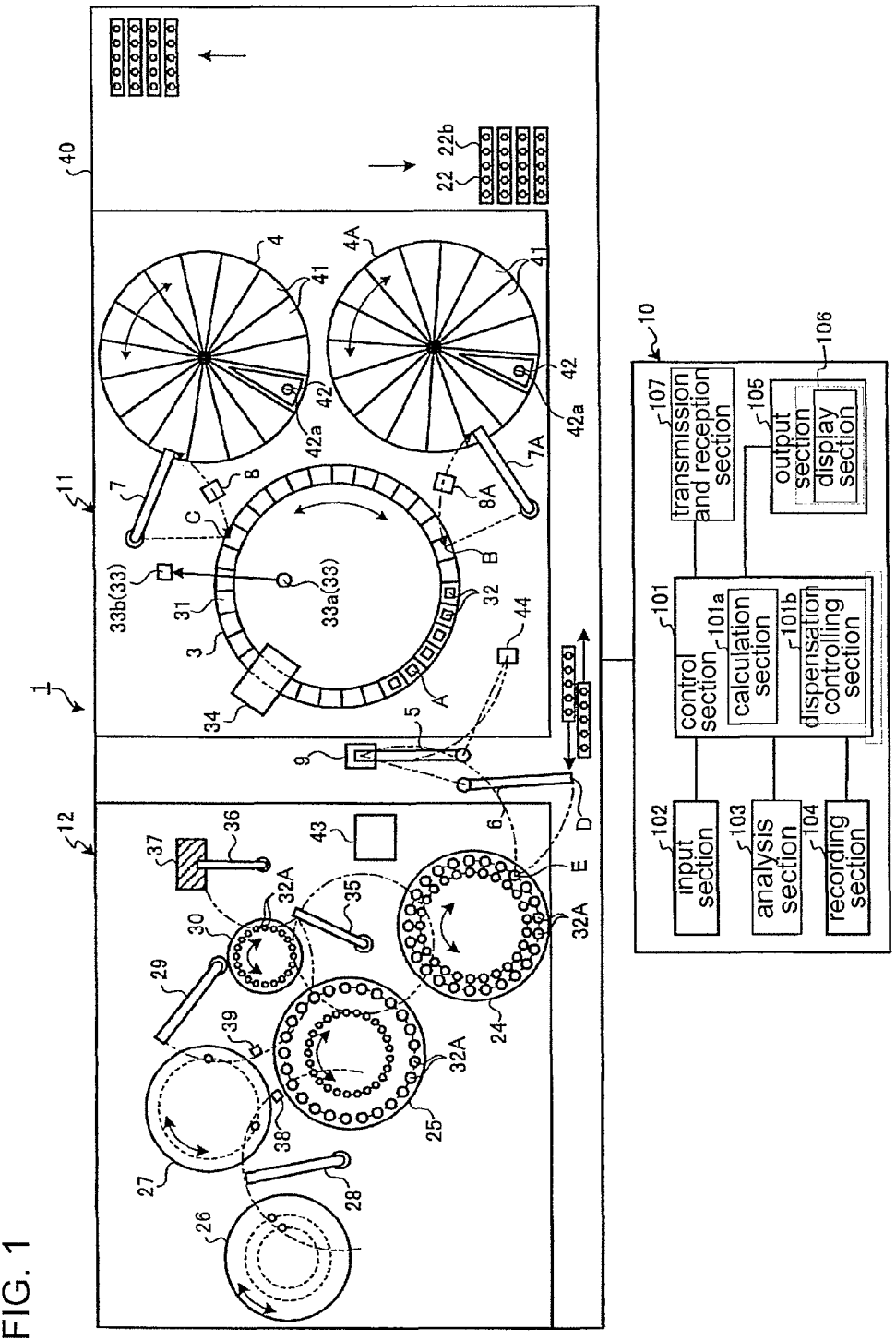
FIG. 1 is a schematic configuration diagram illustrating an automatic analyzer according to Embodiment 1 of the present invention.

1, 1A automatic analyzer
8, 8A, 38, 39, 44, 38A dispensing probe washing apparatus
11 biochemical analysis unit
12 immunological analysis unit
15 analysis unit
22 sample container
22b rack
24, 24A immune reaction table
25 BF table
3 reaction table
30 enzyme reaction table
32, 32A reaction container
33, 37 photometric apparatus
33a light source
33b light receiving section
34 reaction container washing apparatus
35, 36 reaction container transferring sections
4, 4A, 26, 27 reagent table
42, 42A reagent container
42a opening
5, 5' second sample dispensing apparatus
6, 6' first sample dispensing apparatus
70 sample dispensing apparatus
7, 7A, 28, 29 reagent dispensing apparatus
9 aliquot container
13 aliquot container conveying section
14 aliquot container washing section
40 sample container transferring mechanism
41 storage section
43 tip loading unit
46 emergency sample table
47 electrolyte measuring apparatus
48 reaction container disposal opening
60a, 70c disposable tip
60, 70b connection tube
50, 70a dispensing probe
51, 61, 71a, 71b arm
52, 62, 72a, 72b support
53, 63 dispensing probe transferring section
54a, 54b, 64a, 64b tube
55, 65 syringe
55a, 65a cylinder
55b, 65b plunger
56, 66 plunger driving section
57, 67 tank
58, 68 electromagnetic valve
59, 69 pump
10 control mechanism
101 control section
101a calculation section
101b dispensation controlling section
102 input section
103 analysis section
104 recording section
105 output section
106 display section
107 transmission and reception section
L1 pusher fluid
O vertical axis

BEST MODE FOR CARRYING OUT THE INVENTION

Hereinafter, with reference to accompanying figures, an automatic analyzer as well as a sample dispensing method for the automatic analyzer according to the present embodiment of the present invention will be described with examples of an automatic analyzer for analyzing both biochemical assay menu and immunological assay menu with a liquid specimen, such as blood, as a sample. The figures referred in the following description are schematic, and the same object may have a different size, scale or the like in different figures. It should also be noted that the present invention is not limited to the following embodiments, and that identical portions are given the same reference numerals in the description of the figures.

Embodiment 1

FIG. 1 is a schematic configuration diagram illustrating an automatic analyzer according to Embodiment 1 of the present invention. An automatic analyzer 1 is for analyzing a component concentration of a sample by measuring an optical characteristic of a reaction solution obtained by mixing and combining a sample (liquid), such as blood and urine, and a reagent in accordance with an examination menu. The automatic analyzer 1 includes a biochemical analysis unit 11 and an immunological analysis unit 12, functioning as a measuring mechanism for measuring and analyzing light passing through a reactant between a sample and a reagent, or an amount of light emitting from a reaction solution; and a control mechanism 10 for controlling the overall automatic analyzer 1 including the biochemical analysis unit 11 and the immunological analysis unit 12, and for analyzing a measurement result by the measuring mechanism. The automatic analyzer 1 automatically performs analysis of a plurality of samples by the cooperation of the two mechanisms.

First, the biochemical analysis unit 11 will be described. The biochemical analysis unit 11 broadly includes a reaction table 3; reagent tables 4 and 4A; reagent dispensing apparatuses 7 and 7A; and dispensing probe washing apparatuses 8, 8A and 44.

The reaction table 3 is a circular table and includes a plurality of storage sections 31 arranged at regular intervals along the edge of the table. In each of the storage sections 31, a transparent reaction container 32 for housing a sample and a reagent is detachably stored with the opening facing up. In addition, the reaction table 3 rotates in the direction indicated by the arrow in FIG. 1 by a reaction table driving section (not shown) around a vertical line through the center of the reaction table 3 as an axis of rotation. As the reaction table 3 rotates, the transparent reaction container 32 is conveyed to a sample discharge position A, at which a sample is discharged by a second sample dispensing apparatus 5, and is conveyed to reagent discharge positions B and C, at which a reagent is discharged by reagent dispensing apparatuses 7 and 7A. A lid (not shown) capable of opening and closing is provided above the reaction table 3, and a constant temperature tank (not shown) for heating to a temperature at which the reaction between a sample and a reagent is promoted, is provided below the reaction table 3.

A photometric apparatus 33 includes a light source 33*a* and a light receiving section 33*b*. The light source 33*a* outputs an analysis light of a predetermined wavelength. The light receiving section 33*b* measures a beam of light which is an output from the light source 33*a* and is transmitted through a reaction liquid obtained by the combination of a sample and a reagent contained in the reaction container 32. The photometric apparatuses 33 are positioned at positions facing each other in a radius direction, with the storage sections 31 of the reaction table 3 interposed therebetween. The reaction table 3 includes a reaction container washing apparatus 34 for discharging a reaction liquid after the measurement from the reaction container 32 and washing the reaction container 32.

The reagent tables 4 and 4A are a discoid table and include a plurality of storage sections 41 arranged at regular intervals along the edge of the table. In each of the storage sections 41, a reagent container 42 with a reagent contained therein is detachably stored. The reagent container 42 includes an opening section 42*a* which is open upwardly. In addition, the reagent tables 4 and 4A rotate in a direction indicated by the arrow in FIG. 1 by a reagent table driving section (not shown) around a vertical line through the center of the reagent table 4 as an axis of rotation. As the reagent table 4 rotates, the reagent container 42 is conveyed to a reagent suction position at which the reagent is sucked by the reagent dispensing apparatuses 7 and 7A. Herein, a reading apparatus (not shown) is provided at the outer circumference of the reagent dispensing apparatuses 7 and 7A, for reading and outputting reagent information to a control section 101, the reagent information being stored on an information storage medium attached to the reagent container 42. A lid (not shown) capable of opening and closing is provided above the reagent tables 4 and 4A, to prevent the reagent from evaporating or degenerating, and a constant temperature tank (not shown) for cooling the reagent is provided below the reagent tables 4 and 4A.

The reagent dispensing apparatus 7 includes an arm with a dispensing nozzle for sucking and discharging a reagent at a tip portion thereof, capable of ascending and descending in a vertical direction and capable of rotating around a vertical line through a base end section thereof as the central axis. The reagent dispensing apparatus 7 is provided between the reagent table 4 and the reaction table 3 to suck, with the dispensing nozzle, a reagent in the reagent container 42 conveyed to a predetermined position by the reagent table 4, and to turn the arm to dispense the reagent into the reaction container 32 conveyed to a predetermined position by the reaction table 3, for the transferring of the reagent at a predetermined timing into the reaction container 32 on the reaction table 3. The same applies to the reagent dispensing apparatus 7A.

A sample container transferring mechanism 40 transfers a plurality of arranged racks 22*b* by advancing them one by one in the arrowed direction. The rack 22*b* retains a plurality of sample containers 22, each of which contains a sample. The rack 22*b* is advanced by the sample container transferring mechanism 40. When the rack 22*b* is transferred to a sample suction position D, the sample in the sample container 22 is sucked by a first sample dispensing apparatus 6, which will be described later, and the sample is discharged into an aliquot container 9 to subdivide the sample. Subsequently, the sample subdivided into the aliquot container 9 is sucked by the second sample dispensing apparatus 5 and discharged into the reaction container 32, so as to perform sample dispensing for biochemical analysis. The aliquot container 9 is a container for containing a sample for a biochemical assay menu, provided to avoid carry-over from the repeatedly used dispensing probe of the second sample dispensing apparatus 5 into a sample in the sample container 22. The aliquot container 9 is provided at a position above the loci of both probes of the first sample dispensing apparatus 6 and second sample dispensing apparatus 5, and at which the loci intersect with each other. The aliquot container 9 can be any container in which a sample is subdivided and contained from the sample container 22, other than the aliquot container 9 dedicated for the subdividing and dispensing. It is also possible to substitute the reaction container 32 or 32A, which is used for a different purpose in the automatic analyzer 1.

The second sample dispensing apparatus 5 includes an arm with a dispensing probe for sucking and discharging a sample at a tip portion thereof, capable of ascending and descending in a vertical direction and capable of rotating around a vertical line through a base end section thereof as the central axis. The second sample dispensing apparatus 5 sucks a sample in the aliquot container 9 by the dispensing probe, turns the arm, and dispenses the sample into the reaction container 32, which is conveyed to the sample discharge position A by the reaction table 3, for the transferring of the sample to the reaction container 32 on the reaction table 3 at a predetermined timing.

Figure 2:
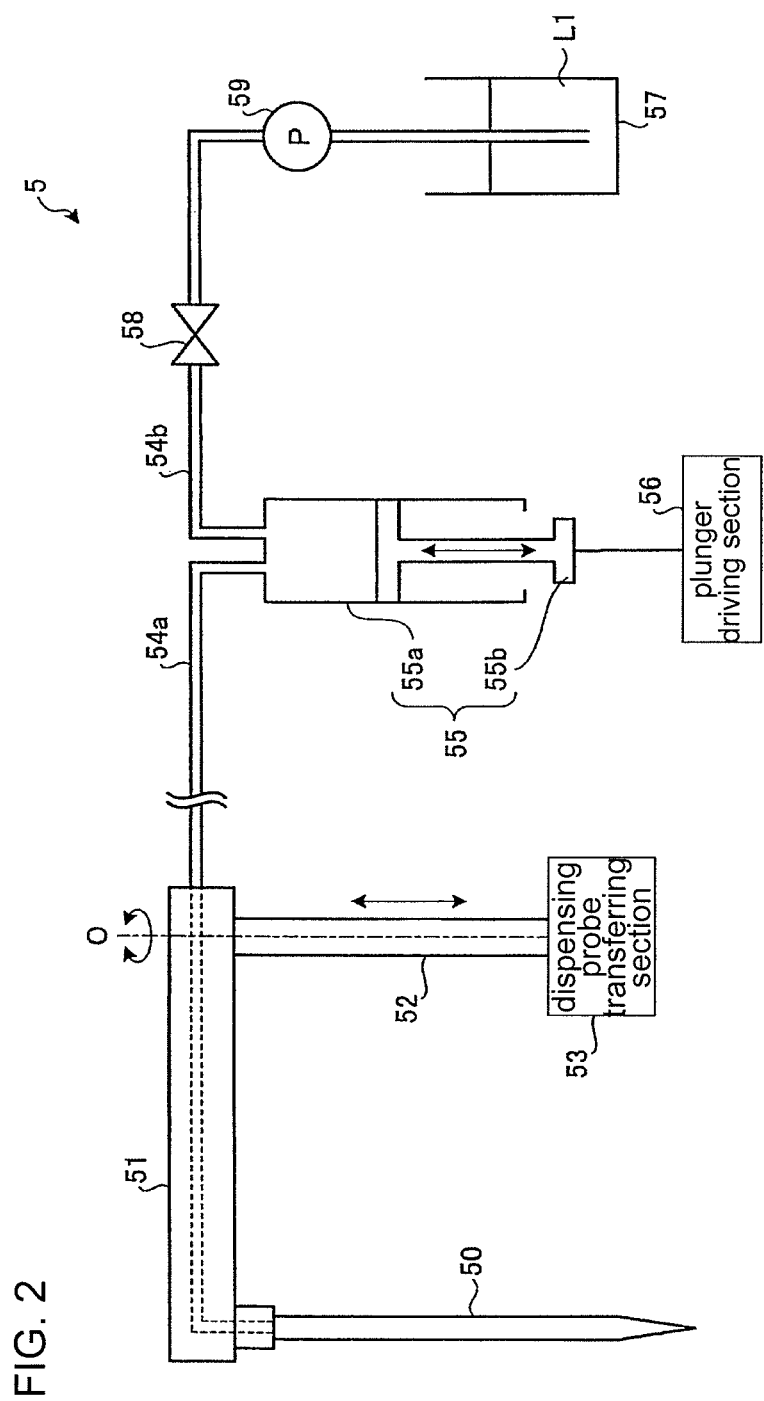
FIG. 2 is a schematic configuration diagram illustrating a second sample dispensing apparatus used in the automatic analyzer in FIG. 1.

FIG. 2 is a schematic configuration diagram of a second sample dispensing apparatus 5. The second sample dispensing apparatus 5 includes a metal dispensing probe 50 as illustrated in FIG. 2. The dispensing probe 50 is stainless steel or the like which is formed into a rod-shape tube and whose tip side is in a tapered-shape. The tip is directed downwardly and an upper base end thereof is attached to the tip of an arm 51. The arm 51 is horizontally positioned and a base end thereof is fixed to an upper end of a support 52. The support 52 is vertically positioned and is rotated by a dispensing probe transferring section 53 around a vertical axis O as the center. As the support 52 is rotated, the arm 51 turns in a horizontal direction to move the dispensing probe 50 in the horizontal direction. The support 52 is also ascended and descended along the vertical axis O by the dispensing probe transferring section 53. As the support 52 ascends or descends, the arm 51 ascends or descends in the vertical direction to ascend or descend the dispensing probe 50 in the vertical (upward and downward) direction, which is the longitudinal direction of the dispensing probe 50.

One end of a tube 54*a* is connected to a base end of the dispensing probe 50. The other end of the tube 54*a* is connected to a syringe 55. The syringe 55 includes a tubular cylinder 55*a* with which the other end of the tube 54*a* is connected, and a plunger 55*b* provided to move inside the cylinder 55*a* back and forth in such a manner to slide on an inner wall surface of the cylinder 55*a*. The plunger 55*b* is connected to a plunger driving section 56. The plunger driving section 56 is configured with, for example, a linear motor, and configured to perform the back and forth movement of the plunger 55*b* relative to the cylinder 55*a*. One end of the tube 54*b* is connected with the cylinder 55*a* of the syringe 55. The other end of the tube 54*a* is connected to a tank 57 for containing a pusher fluid L1. In addition, an electromagnetic valve 58 and a pump 59 are connected in the middle of the tube 54b. An incompressible fluid, such as distilled water or degassed water, is used as the pusher fluid L1. The pusher fluid L1 is also used as a washing fluid for washing the inside of the dispensing probe 50.

The second sample dispensing apparatus 5 drives the pump 59 and opens the electromagnetic valve 58, so that the pusher fluid L1 contained in the tank 57 is filled inside the cylinder 55a of the syringe 55 through the tube 54b, and is further filled to the tip of the dispensing probe from the cylinder 55a through the tube 54a. The electromagnetic valve 58 is closed and the pump 59 is stopped in such a state where the pusher fluid L1 fills up to the tip of the dispensing probe 50. In a case when the suction of a sample or a reagent is performed, the plunger driving section 56 is driven to move the plunger 55b backwards relative to the cylinder 55a, so that a suction pressure is applied to the tip portion of the dispensing probe 50 through the pusher fluid L1, causing the sample or reagent to be sucked by the suction pressure. On the other hand, in a case when the discharge of the sample or reagent is performed, the plunger driving section 56 is driven to move the plunger 55b forwards relative to the cylinder 55a, so that a discharge pressure is applied to the tip portion of the dispensing probe 50 through the pusher fluid L1, causing the sample or reagent to be discharged by the discharge pressure.

The dispensing probe washing apparatus 44 is provided at a position in the middle of the locus of the horizontal movement made by the dispensing probe 50 of the second sample dispensing apparatus 5. In order to prevent carry-over between samples, the dispensing probe 50 is washed by the dispensing probe washing apparatus 44 every time the dispensing probe 50 dispenses a sample. The dispensing probe 50 is dipped into a washing fluid stored in a washing tank of the dispensing probe cleaning apparatus 44, or an external wall surface of the dispensing probe 50 is washed by spraying pressured shower or the like of the washing fluid. The internal wall surface is washed by spouting the pusher fluid L1 from the dispensing probe 50. The same applies to dispensing probe washing apparatuses 8 and 8A.

In the biochemical analysis unit 11 with such a structure, the rack 22b containing the sample container 22 is conveyed to the sample suction position D by the sample container transferring mechanism 40, and subsequently, a sample is subdivided and dispensed into the aliquot container 9 by the first sample dispensing apparatus 6, the sample inside the aliquot container 9 is sucked by the second sample dispensing apparatus 5, and the sample is discharged to the reaction container 32 in which a reagent is dispensed. The reagent is further dispensed into the reaction container 32, and the sample and the reagent are stirred and combined while being conveyed along the edge of the reaction table 3. The sample and the reagent subsequently pass between the light source 33a and the light receiving section 33b. At the same time, an analysis light, an output from the light source 33a which is transmitted through the reaction liquid, is measured by the light receiving section 33b so that component concentration and the like are analyzed. For the reaction container 32 which went through the analysis process, the reaction liquid after the measurement is discharged, and the reaction container 32 is washed, by the reaction container washing apparatus 34. Subsequently, the reaction container 32 will be used again for sample analysis.

Next, the immunological analysis unit 12 will be described. The immunological analysis unit 12 broadly includes an immune reaction table 24, a BF table 25, reagent tables 26 and 27, reagent dispensing apparatuses 28 and 29, an enzyme reaction table 30, a photometric apparatus 37, reaction container transferring sections 35 and 36, dispensing probe washing apparatuses 38 and 39, and a tip loading unit 43.

Many of the elements of the immunological analysis unit 12 are common to those of a biochemical analysis unit. Thus, characteristic elements in the immunological analysis unit will be described hereinafter.

The reagent tables 26 and 27 store a plurality of reagent containers, and each of the reagent containers contains: a reagent used for analysis of immunological assay menu, including magnetic particles obtained by solidifying a reaction substance specifically binding to an antigen or antibody in an analysis-object sample; a labeled substance (e.g., enzyme) specifically binding to an antigen or antibody bound to magnetic particles; or a substrate solution including a substrate which emits light by an enzymatic reaction with a labeled substance.

The immune reaction table 24 includes reaction lines for the reaction of a sample and a predetermined reagent in the reaction container 32, and includes two reaction lines, i.e., an outer circumference line for the first reaction between a sample and a magnetic particle reagent, and an internal circumference line for the second reaction between a sample and a labeled reagent. Each reaction line includes a plurality of reaction container housing sections formed therein for housing a reaction container 32A. The immune reaction table 24 is capable of moving rotationally in the arrowed direction in FIG. 1, around a vertical line through the center of the immune reaction table 24 as an axis of rotation. The immune reaction table 24 transfers the reaction container 32A housed in the reaction container housing section (not shown) of the immune reaction table 24, to a sample discharge position E or the like at a predetermined timing.

The BF table 25 performs a BF washing process, in which BF (bound-free) separation is performed for separating unreacted substance in a sample or a reagent by sucking and discharging a predetermined washing fluid. The BF table 25 is capable of moving rotationally in the arrowed direction in FIG. 1, around a vertical line through the center of the BF table 25 as an axis of rotation. The BF table 25 transfers the reaction container 32A placed on the BF table 25 to a predetermined position at a predetermined timing. The BF table 25 includes a magnetic collection mechanism for magnetically collecting magnetic particles needed for BF separation, a BF washing section with a BF washing probe for performing BF separation by discharging and sucking a BF fluid into and from a reaction container, and a stirring mechanism for dispersing magnetically collected magnetic particles.

The enzyme reaction table 30 is a reaction line for performing an enzymatic reaction step, which enables a substrate to emit light, the substrate being in a substrate solution dispensed in the reaction container 32A. The enzyme reaction table 30 includes a reaction container housing section formed therein for housing the reaction container 32A in the periphery thereof. The enzyme reaction table 30 is capable of moving rotationally in the arrowed direction in FIG. 1, around a vertical line through the center of the enzyme reaction table 30 as an axis of rotation. The enzyme reaction table 30 transfers the reaction container 32A housed in the enzyme reaction table 30 to a predetermined position at a predetermined timing.

The reaction container transferring sections 35 and 36 each include an arm, which is capable of ascending and descending in a vertical direction and capable of rotating around a vertical line through a base end section thereof as the central axis, and which transfers the reaction container 32A containing a sample and a predetermined reagent at a predetermined timing to a predetermined position of the immune reaction table 24, the BF table 25, the enzyme reaction table 30, the photometric apparatus 37, a reaction container supply section (not shown) and a reaction container disposal section.

The first sample dispensing apparatus 6 subdivides and dispenses a sample in a sample container 22 conveyed to the sample suction position D by the sample container transferring mechanism 40, into an aliquot container 9 as a sample for biochemical analysis. In a case where immunological assay menu is ordered for the same sample, the first sample dispensing apparatus 6 sucks the sample from a sample container 22 for the immunological assay menu, and discharges the sample into the reaction container 32A retained on the immune reaction table 24 at the sample discharge position E.

Figure 3:
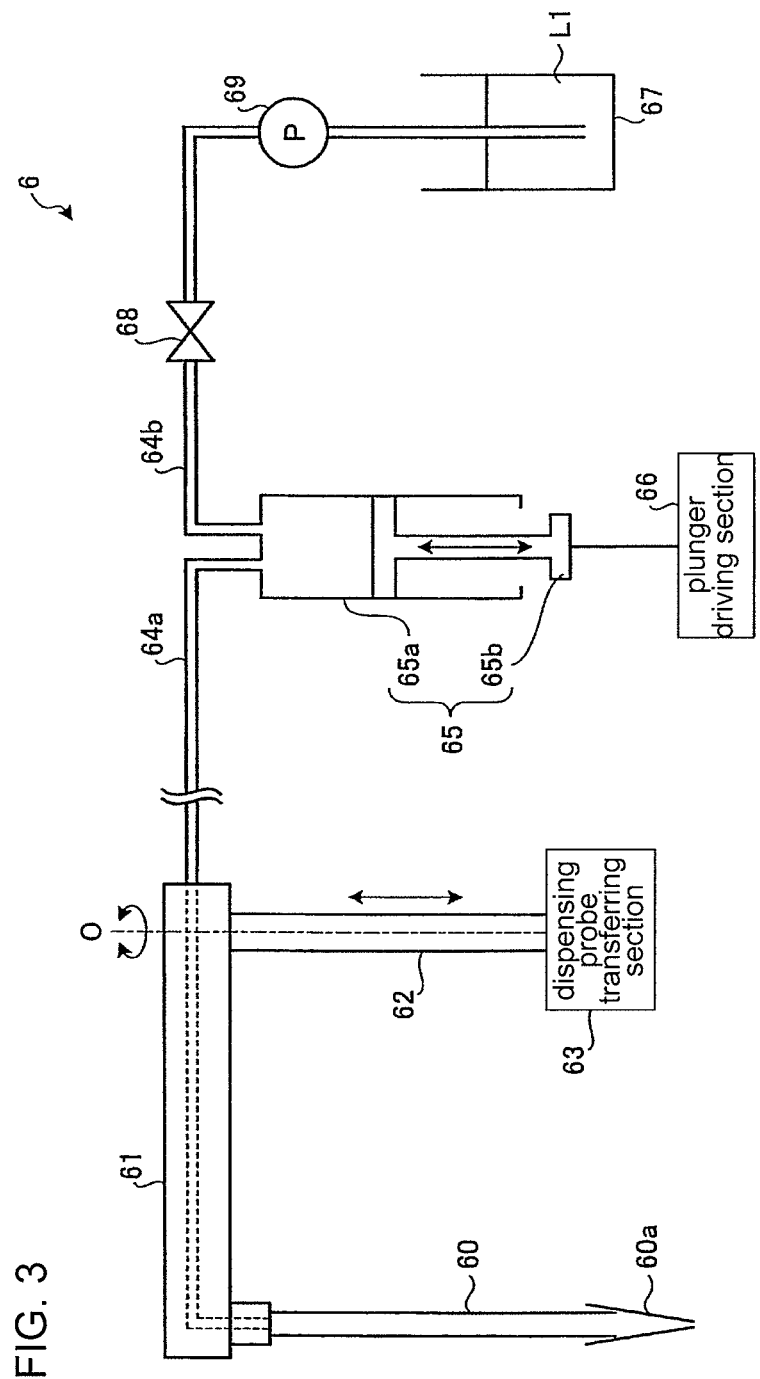
FIG. 3 is a schematic configuration diagram illustrating a first sample dispensing apparatus used in the automatic analyzer in FIG. 1.

As illustrated in FIG. 3, the first sample dispensing apparatus 6 includes a disposable tip 60a for sucking and discharging a sample, attached to a tip portion of a connection tube 60, and capable of ascending and descending in a vertical direction and capable of rotating around a vertical line through a base end section thereof as the central axis. The first sample dispensing apparatus 6 has the same structure as the second sample dispensing apparatus 5, except for the disposable tip 60a attached to the tip portion of the connection tube 60.

In the tip loading unit 43, a tip case with a plurality of disposable tips arranged therein is provided, and the disposable tip 60a is supplied from this case. The disposable tip 60a is a disposable sample tip, which is attached to the tip portion of the connection tube 60 of the first sample dispensing apparatus 6 and is replaced for each sample dispensing, in order to prevent carry-over during the measurement of immunological assay menu. In addition, in the tip loading unit 43, the detaching of the disposable tip 60a is performed, in addition to the attaching of the disposable tip 60a to the connection tube 60, and a disposable box for used disposable tip 60a is provided therein.

In the immunological analysis unit 12 with such a structure, the rack 22b containing the sample container 22 is conveyed to the sample suction position D by the sample container transferring mechanism 40, and subsequently, the sample in the sample container 22 is dispensed into the reaction container 32A by the first sample dispensing apparatus 6 to which the disposable tip 60a is attached. A reagent, such as magnetic particles, a labeled substance, and a substrate solution, is further dispensed into the reaction container 32A with an interposition of a step for removing an unreacted substance or the like by BF washing or the like; and an interaction among the sample, an immune complex generated by the reaction of reagents, and the substrate is formed with one another. As a result, the emission of light from the substrate is measured by the photometric apparatus 37.

Next, the control mechanism 10 will be described. As illustrated in FIG. 1, the control mechanism 10 includes a control section 101, an input section 102, an analysis section 103, a recording section 104, an output section 105, and a transmission and reception section 107. The respective sections included in the control mechanism 10 are electrically connected with the control section 101. The control section 101 is constituted of a CPU and the like, for controlling the processing and operation of the respective sections in the automatic analyzer 1. The control section 101 performs a predetermined input and output control on information input to and output from the respective elements, and also performs predetermined information processing on the information. The control section 101 includes a calculation section 101a and a dispensation controlling section 101b. The calculation section 101a adds up and calculates the amount of samples required for biochemical analysis, which is an assay menu with a low carry-over avoiding level, for each analysis sample. The dispensation controlling section 101b performs the following controls: when a retest is necessary for immunological assay menu, which is assay menu with a high carry-over avoiding level, a sample is dispensed from the sample container 22 to the reaction container 32A using the first sample dispensing apparatus 6 to which a new disposable tip 60a is attached; and when a retest is conducted for biochemical assay menu, which is assay menu with a low carry-over avoiding level, a sample is subdivided into the aliquot container 9 from the sample container 22 by the first sample dispensing apparatus 6 to which a new disposable tip 60a is attached, and subsequently the sample is dispensed from the aliquot container 9 by the second sample dispensing apparatus 5. The analysis section 103 is connected to the photometric apparatuses 33 and 37 of each unit through the control section 101. The analysis section 103 analyzes component concentration and the like of a sample based on an amount of light, and outputs an analysis result into the control section 101. The input section 102 is a part for performing an input operation of an examination menu and the like into the control section 101; and a keyboard, a mouse or the like is used for the input section 102.

The recording section 104 is constituted of a hard disk for magnetically storing information, and a memory for loading, and electrically storing, various programs from the hard disk when the automatic analyzer 1 performs processing, the programs being associated with the processing. The recording section 104 stores various pieces of information including an analysis result of a sample and the like. The recording section 104 may include a supplemental storing apparatus capable of reading information stored on a storage medium, such as CD-ROM, DVD-ROM, PC card and the like. The recording section 104 also stores a sample amount required for the analysis of biochemical assay menu calculated by the calculation section 101a, for each sample.

The output section 105 is constituted of a printer, a speaker and the like, for outputting various types of information relating to analysis, under the control of the control section 101. The output section 105 includes a display section 106 constituted of a display and the like. The display section 106 is for displaying analysis content, alarm and the like, and a display panel or the like is used for the display section 106. The input section 102 and display sect ion 106 may be actualized with a touch panel. The transmission and reception section 107 has a function as an interface for performing transmission and reception of information in accordance with a predetermined format via a communication network (not shown).

In addition, the control section 101 is connected with respective sections of the first sample dispensing apparatus 6 and the second sample dispensing apparatus 5 described above, dispensing probe transferring sections 53 and 63, plunger driving sections 56 and 66, electromagnetic valves 58 and 68 and pumps 59 and 69. The control mechanism 10 also controls the operational processing by the first sample dispensing apparatus 6 and second sample dispensing apparatus 5.

In the automatic analyzer 1 with such a structure, an examination order is received by the input section 102, and subsequently, a sample amount required for the analysis of biochemical assay menu is calculated by adding-up each sample by the calculation section 101a, and the amount of the sample calculated is sucked from the sample container 22 by the first sample dispensing apparatus 6 and is subdivided and dispensed into the aliquot container 9. The sample for biochemical assay menu is sucked from the aliquot container 9 by the second sample dispensing apparatus 5 and is discharged to the reaction container 32. The dispensation of the sample for immunological assay menu is directly sucked from the sample container 22 by the first sample dispensing apparatus 6 and is discharged to the reaction container 32A. As the sample is dispensed by the second sample dispensing apparatus 5 and the first sample dispensing apparatus 6, analysis is conducted in the biochemical analysis unit 11 and the immunological analysis unit 12. When a retest is necessary depending on an analysis result, the subdividing and dispensing or the dispensing for immunological analysis is again performed from the sample container 22 by the first sample dispensing apparatus 6, and the dispensing for biochemical analysis is performed from the aliquot container 9 after the subdividing and dispensing, by the second sample dispensing apparatus 5. Thus, with regard to the second sample dispensing apparatus 5, which tends to cause carry-over, it is possible to avoid carry-over completely even in a case where a retest is necessary, only by not dispensing a sample directly from the sample container 22. Further, according to Embodiment 1 of the present invention, it becomes possible to perform a parallel dispensing by the second sample dispensing apparatus 5 and first sample dispensing apparatus 6, enabling a significant improvement on processing capacity.

Figure 4:
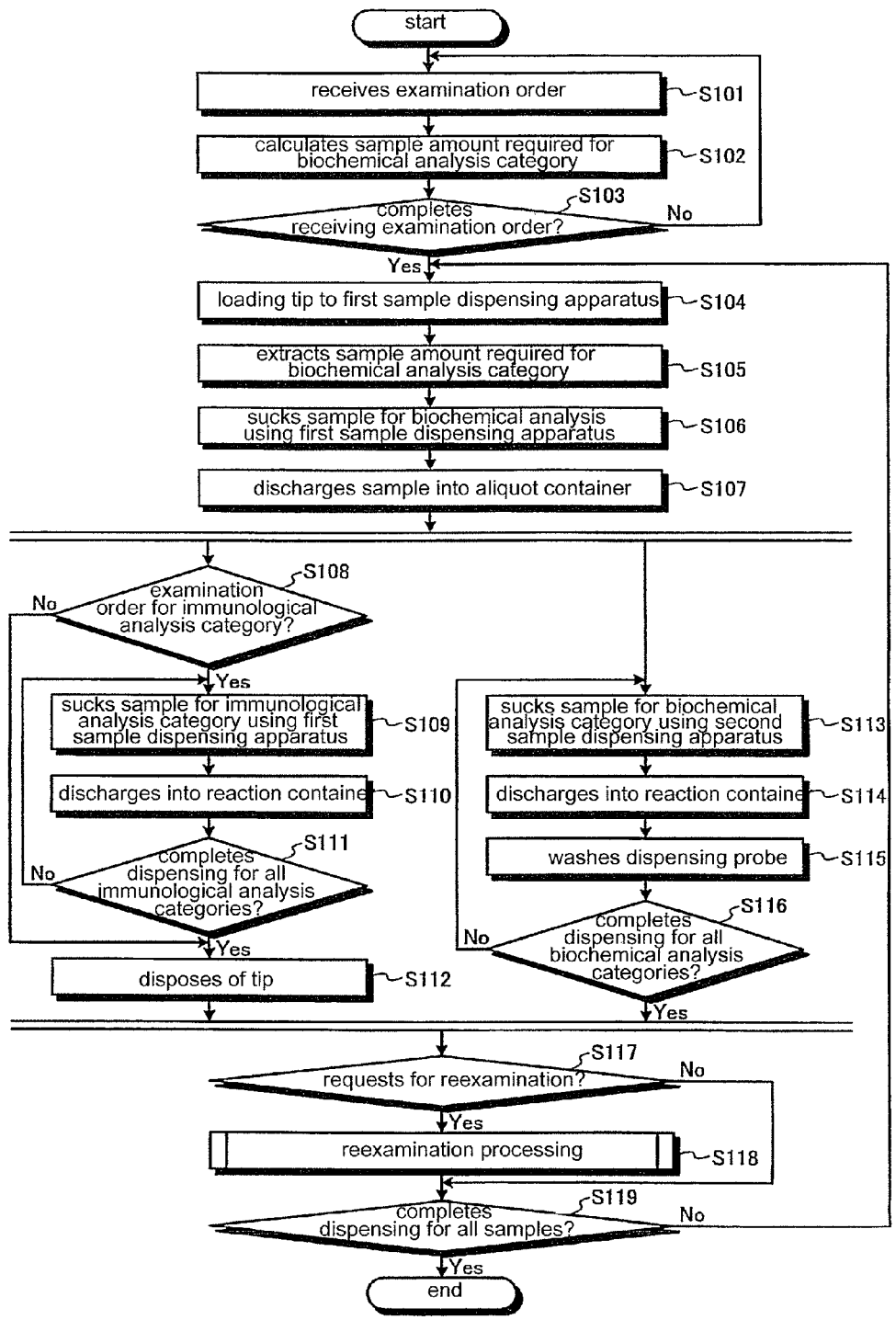
FIG. 4 is a flow chart illustrating processing steps of a dispensing operation by the automatic analyzer according to Embodiment 1.
Figure 5:
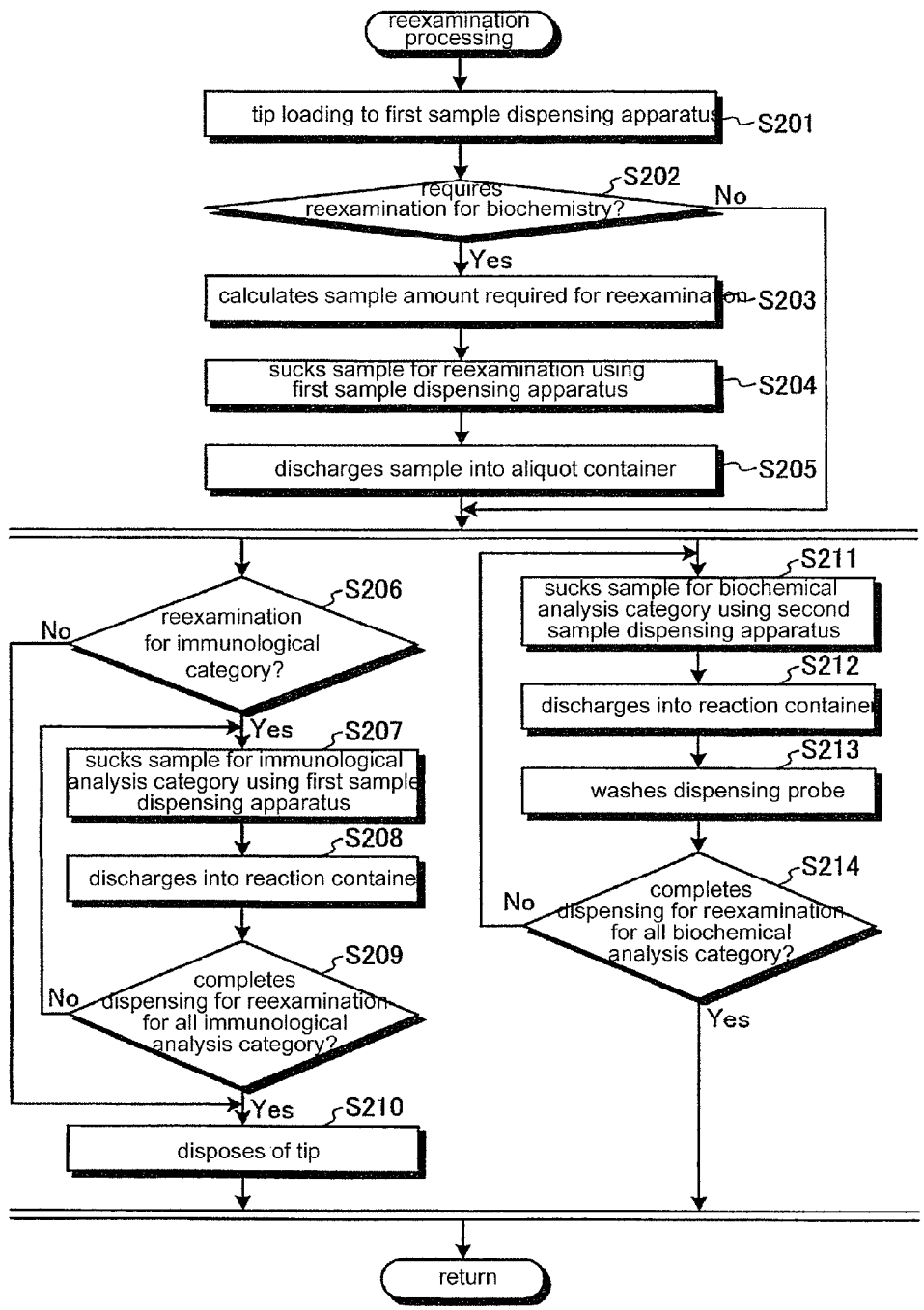
FIG. 5 is a flow chart illustrating processing steps of a retest illustrated in FIG. 4.

Next, a sample dispensing method according to Embodiment 1 of the present invention will be described in detail with reference to FIGS. 4 and 5. FIG. 4 is a flow chart illustrating processing steps of a dispensing operation by the automatic analyzer 1 according to Embodiment 1. FIG. 5 is a flow chart illustrating processing steps of retest processing illustrated in FIG. 4. Further, as illustrated in FIG. 4, an examination order is received for each sample (step S101). The examination order is received through the input section 102 based on an examination order table consisting of sample numbers and assay menu. The calculation section 101a adds up and calculates a sample amount required for the analysis of biochemical assay menu for each received sample (step S102). A sample amount required for each of the assay menu is stored in the recording section 104, as a sample dispensing amount or a sample sucking amount for each of all the assay menu, and therefore, the sample dispensing amount or sample sucking amount of biochemical assay menu with an examination order is extracted from the recording section 104 under the control of the control section 101. Subsequently, the amount is added up and calculated by the calculation section 101a and stored in the recording section 104. Herein, the sample dispensing amount means a sample amount required for actual analysis, and the sample sucking amount means an amount obtained by adding a sample amount sucked extra in consideration of the diluting of the sample by the pusher fluid, to a sample amount required for analysis.

The reception of an examination order and calculation of a sample amount are repeated until the reception of all of the examination orders is completed (step S103, No). Upon completion of the reception of all of the examination orders (step S103, Yes), the disposable tip 60a is attached to the connection tube 60 of the first sample dispensing apparatus 6 in the tip loading unit 43 under the control of the control section 101 (step S104). After the attachment of the disposable tip 60a, the sample amount required for all the analysis of the biochemical assay menu of a sample to be analyzed is extracted from the recording section 104 (step S105); the sample amount being calculated at the step S102; the added-up sample amount is sucked from the sample container 22 by the first sample dispensing apparatus 6 (step S106); and the sample is discharged into the aliquot container 9 (step S107).

Subsequently, with regard to the dispensing of the sample for immunological assay menu, the dispensing is performed from the sample container 22 by the first sample dispensing apparatus 6. With regard to the dispensing of the sample for biochemical assay menu, the sample is dispensed by the second sample dispensing apparatus 5 from the aliquot container 9, in which the sample is subdivided and dispensed. Since the sample dispensing for immunological assay menu as well as the sample dispensing for biochemical assay menu are performed in parallel for the same sample, it becomes possible to improve the processing capacity. First, the sample dispensing for immunological assay menu will be described. It is confirmed whether or not an examination order for immunological assay menu is made for a sample to be dispensed (step S108). If the examination order is made (step S108, Yes), then a sample for immunological assay menu is sucked from the sample container 22 by the first sample dispensing apparatus 6 (step S109), and the sample is discharged into the reaction container 32A retained on an immune reaction table 24 (step S110). It is confirmed as to whether the dispensing for all of the immunological assay menu is completed for the same sample (step S111). If the dispensing is not completed (step S111, No), then the steps S109 to S110 are repeated. If the dispensing is completed (step S111, Yes), then the disposable tip 60a attached is detached by the tip loading unit 43, and the disposable tip 60a is disposed (step S112). Even if an examination order is not made (step S108, No), the disposable tip 60a attached is detached by the tip loading unit 43, and the disposable tip 60a is disposed in a similar manner (step S112). A reagent is already dispensed in the reaction container 32A to which the sample has been discharged, the reagent including magnetic particles obtained by solidifying a reaction substance which reacts with an analysis object. After the dispensing of the sample, reaction container 32A is conveyed to the BF table 25 by the reaction container transferring section 35 to perform BF washing thereon. After the dispensing of a labeled substance, BF washing, and the dispensing of a substrate solution, the reaction container 32A is conveyed to the enzyme reaction table 30 by the reaction container transferring section 35, and emission of light is measured by the photometric apparatus 37.

On the other hand, with regard to the sample dispensing for biochemical assay menu, the sample is sucked from the aliquot container 9, in which the sample is subdivided and dispensed, by the second sample dispensing apparatus 5 (step S113), and the sample is discharged into the reaction container 32 retained on the reaction table 3 (step S114). The dispensing probe 50 is washed by the dispensing probe washing apparatus 44 (step S115), and subsequently, it is confirmed as to whether the dispensing for all of the biochemical assay menu is completed for the same sample (step S116). If the dispensing is not completed (step S116, No), then the steps S113 to S115 are repeated. If the dispensing is completed (step S116, Yes), then the method advances to a subsequent step. A first reagent is already dispensed in the reaction container 32 in which the sample has been dispensed. After the sample dispensation, a second reagent is dispensed, and absorbance is measured by the photometric apparatus 33. The reaction container 32 used in the reaction is washed by the reaction container washing apparatus 34, and is used again. It is also possible to wash and reuse the aliquot container 9 by a washing apparatus (not shown). Alternatively, it is also possible to use a disposable aliquot container 9.

When all of the dispensing for the immunological assay menu and the biochemical assay menu are completed, it is confirmed as to whether a retest is requested for the same sample (step S117). If a retest order is made (step S117, Yes), then a processing step for retest, to be described later, is performed (step S118). If the retest order is not made (step S117, No), then it is confirmed as to whether or not all of the sample dispensing is completed (step S119). If all of the sample dispensing is not completed (step S119, No), then the dispensing of the sample is performed again at the step S104. If all of the sample dispensing is completed (step S119, Yes), then the sample dispensing process is completed.

Next, retest processing will be described with reference to FIG. 5. In the tip loading unit 43, the disposable tip 60a is attached to the connection tube 60 of the first sample dispensing apparatus 6, as illustrated in FIG. 5 (step S201). After the attaching of the disposable tip 60a, it is confirmed as to whether or not biochemistry is included in assay menu needed to be reexamined (step S202). If biochemical assay menu need to be reexamined (step S202, Yes), then a sample amount for biochemical assay menu needed to be reexamined is calculated by the adding-up (step S203). Subsequently, an added-up sample amount is sucked from the reaction container 22 by the first sample dispensing apparatus 6 (step S204), and the sample is discharged to the aliquot container 9 (step S205) If the biochemical assay menu does not need to be reexamined (step S202, No), then the method moves to a step S206.

Subsequently, the method moves to dispensation processing for retest. Sample dispensing for the retest of immunological analysis is performed in parallel with sample dispensing for the retest of biochemical assay menu. First, with regard to the dispensing for immunological assay menu, it is confirmed as to whether or not a retest for immunological assay menu is necessary (step S206). If the immunological assay menu needs to be reexamined (step S206, Yes), then the sample for immunological assay menu retest is sucked from the sample container 22 by the first sample dispensing apparatus 6 (step S207). On the other hand, if the immunological assay menu does not need to be reexamined (step S206, No), then the method moves to a step S210. The sample for immunological assay menu retest is sucked (step S207), and subsequently, the sample is discharged into the reaction container 32A retained on the immune reaction table 24 (step S208). It is confirmed as to whether or not the dispensing for all of the immunological assay menu retest is completed for the same sample (step S209). If the dispensing is not completed (step S209, No), then the steps S207 to S208 are repeated. If the dispensing is completed (step S209, Yes), then the disposable tip 60a attached is detached by the tip loading unit 43, and is disposed (step S210).

On the other hand, with regard to the sample dispensing for the retest of biochemical assay menu, the sample for biochemical assay menu retest is sucked from the aliquot container 9 by the second sample dispensing apparatus 5 (step S211), and the sample is discharged into the reaction container 32 retained on the reaction table 3 (step S212). The dispensing probe 50 is washed by the dispensing probe washing apparatus 44 (step S213), and subsequently, it is confirmed as to whether the dispensing for the retest of all of the biochemical assay menu is completed for the same sample (step S214). If the dispensing is not completed (step S214, No), then the steps S211 to S213 are repeated. If the dispensing is completed (step S214, Yes), then the sample dispensing for retest is completed.

Figure 6:
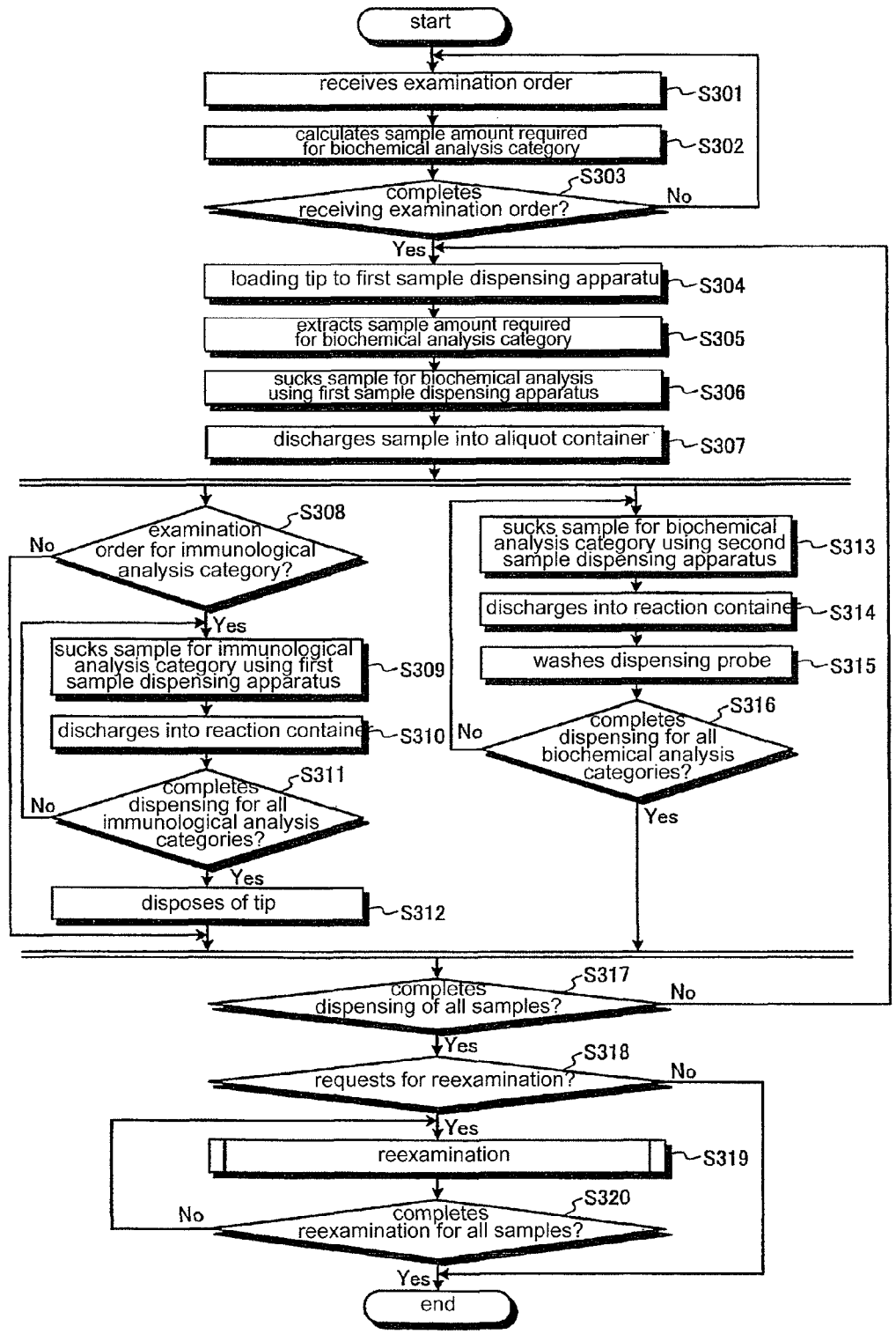
FIG. 6 is a chart illustrating an examination order according to Embodiment 1, 2, 3 or 4.

The steps of the dispensation processing of the automatic analyzer according to Embodiment 1 confirm whether or not a request is made for retest, for each sample. However, as a variation example, steps S301 to S316 are performed in a similar manner as the steps S201 to S216, as illustrated in FIG. 6. Further, after all the sample dispensing ordered for examination is completed (step S317, Yes), it is confirmed as to whether a request for retest is made (step S318). If a request for retest is made (step S318, Yes), then the retest processing described above is performed (step S319). If a request for retest is not made (step S318, No), then the sample dispensing processing is completed. It is also possible to conduct a retest successively until the retest for all of the samples requested for retest is completed (step S320, Yes). According to the present variation example, the dispensing processing can be advanced even if it is not possible to promptly determine whether or not a retest is requested, making it possible to further improve the processing capacity.

In addition, in the sample dispensing method according to Embodiment 1, a sample amount required for biochemical assay menu is added up and calculated with regard to all of the samples ordered to be examined (step S102), and the sample amount calculated is subdivided and dispensed into the aliquot container 9 by the first sample dispensing apparatus 6 (steps S104 to S107). However, it is also possible to perform as follows: it is confirmed as to whether or not immunological assay menu is ordered, and the subject processing is performed only if the immunological assay menu is ordered, while the sample dispensing is directly performed from the sample container 22 by the second sample dispensing apparatus 5 if the immunological assay menu is not ordered.

Figure 7:
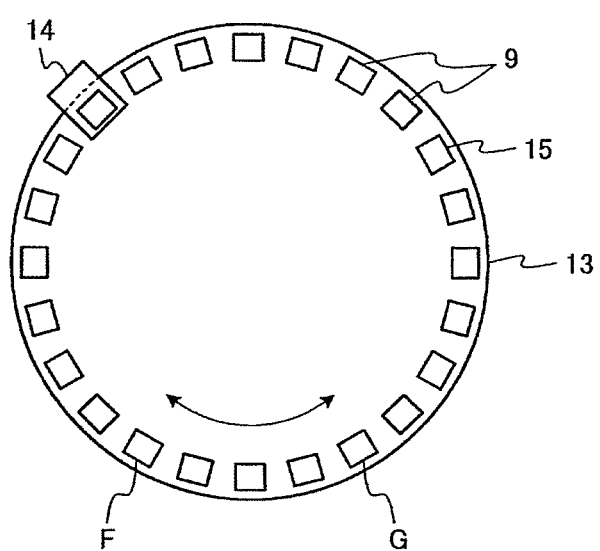
FIG. 7 is a schematic configuration diagram of an aliquot container conveying apparatus, which is a variation example of Embodiment 1.

The automatic analyzer 1 may also include an aliquot container conveying section 13 as illustrated in FIG. 7. The aliquot container conveying section 13 includes a discoid table and includes a plurality of storage sections 15 arranged at regular intervals along the edge of the table. The aliquot container 9 is detachably stored in each of the storage sections 15. In addition, the aliquot container conveying section 13 rotates in the direction indicated by the arrow in FIG. 7 by a reagent table driving section (not shown) around a vertical line through the center of the aliquot container conveying section 13 as an axis of rotation. The aliquot container conveying section 13 transfers the aliquot container 9 to a sample discharge position F by the first sample dispensing apparatus 6 and to a sample suction position G by the second sample dispensing apparatus 5. The aliquot container conveying section 13 may include an aliquot container washing section 14 for reusing the aliquot container 9.

Figure 8:
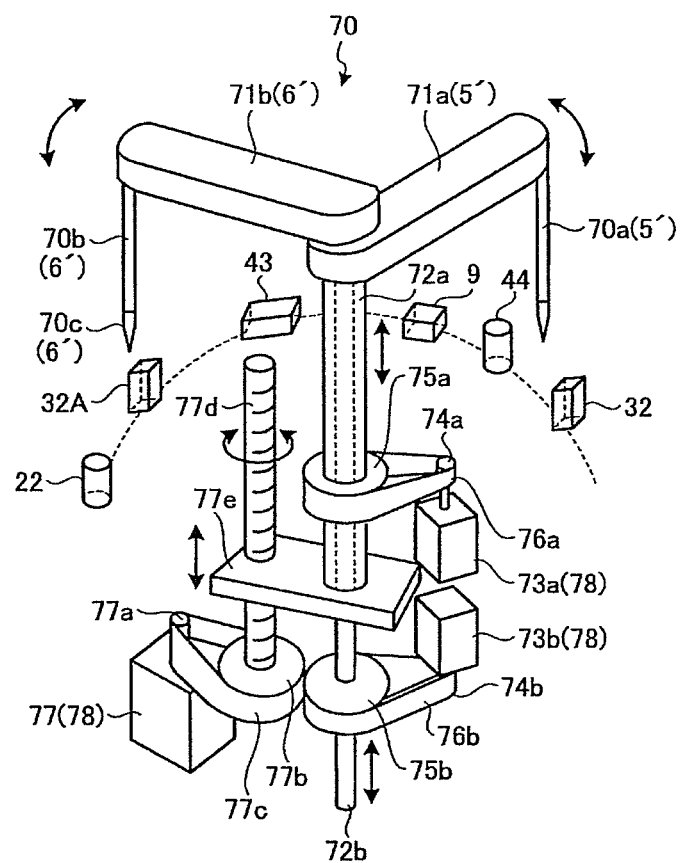
FIG. 8 is a perspective view of a sample dispensing apparatus with a coaxial twin arm, which is a variation example of Embodiment 1.

In Embodiment 1, while the first sample dispensing apparatus 6 and the second sample dispensing apparatus 5 are independently provided, it is further possible to use a sample dispensing apparatus 70 with a coaxial twin arm unit as illustrated in FIG. 8. The sample dispensing apparatus 70 includes arms 71a and 71b, which pivot in a horizontal direction over the locus connecting the sample container 22, reaction containers 23 and 32A, tip loading unit 43, aliquot container 9, dispensing probe washing apparatus 44 and the like. A dispensing probe 70a and a connection tube 70b are supported by the arms 71a and 71b, and a disposable tip 70c is loaded to the tip of the connection tube 70b. In the example in FIG. 8, the arm 71a for supporting the dispensing probe 70a is a second sample dispensing apparatus 5' for loading a reusable metal probe. Also, the arm 71b for supporting the connection tube 70b, to which the disposable tip 70c is loaded, is a first sample dispensing apparatus 6'. The sample dispensing apparatus 70 includes supports 72a and 72b for supporting the arms 71a and 71b respectively. In order to perform the ascending and descending simultaneously and the rotating independently, the two arms 71a and 71b include a driving mechanism 78, which includes rotation motors 73a and 73b and an ascent and descent motor 77. With regard to the rotation motors 73a and 73b, timing belts 76a and 76b are wound around wheels (not shown) attached to rotating shafts 74a and 74b and wheels 75a and 75b attached to the supports 72a and 72b. The ascent and descent motor 77 rotates a rotating shaft 77a through a timing belt 77c to move an ascent and descent block 77e up and down along a screw shaft 77d. The timing belt 77c is wound around a wheel attached to the rotating shaft 77a and a wheel 77b attached to the lower end of the screw shaft 77d. The ascent and descent block 77e herein is attached to the lower end of the support 72a to support the supports 72a and 72b, and the ascent and descent block 77e, together with the screw shaft 77d, constitutes a ball screw.

Since the arms 71a and 71b ascend and descend simultaneously, it is preferable to determine the positions at the ascent and descent. When the dispensing probe 70b is positioned above the sample container 22 and ascends or descends, the dispensing probe 70a is positioned above the aliquot container 9; when the dispensing probe 70b is above the aliquot container 9 or reaction container 32A, the dispensing probe 70a is positioned above the reaction container 32; when the dispensing probe 70b is above the tip loading unit 43, the dispensing probe 70a is positioned above the dispensing probe washing apparatus 44, and the ascending or descending is performed simultaneously. It is preferable to use the sample dispensing apparatus 70 as illustrated in FIG. 8 so that not only the space efficiency, but also the maintainability and the handling by users, can be improved.

Embodiment 2

Embodiment 2 is a case where an aliquot container for subdividing a sample for biochemical analysis is provided in an integrated apparatus including, in one analysis unit, a biochemical analysis module for performing a biochemical analysis, and an immunological analysis module for performing an immunological analysis. Hereinafter, Embodiment 2 will be described with reference to FIG. 9.

Figure 9:
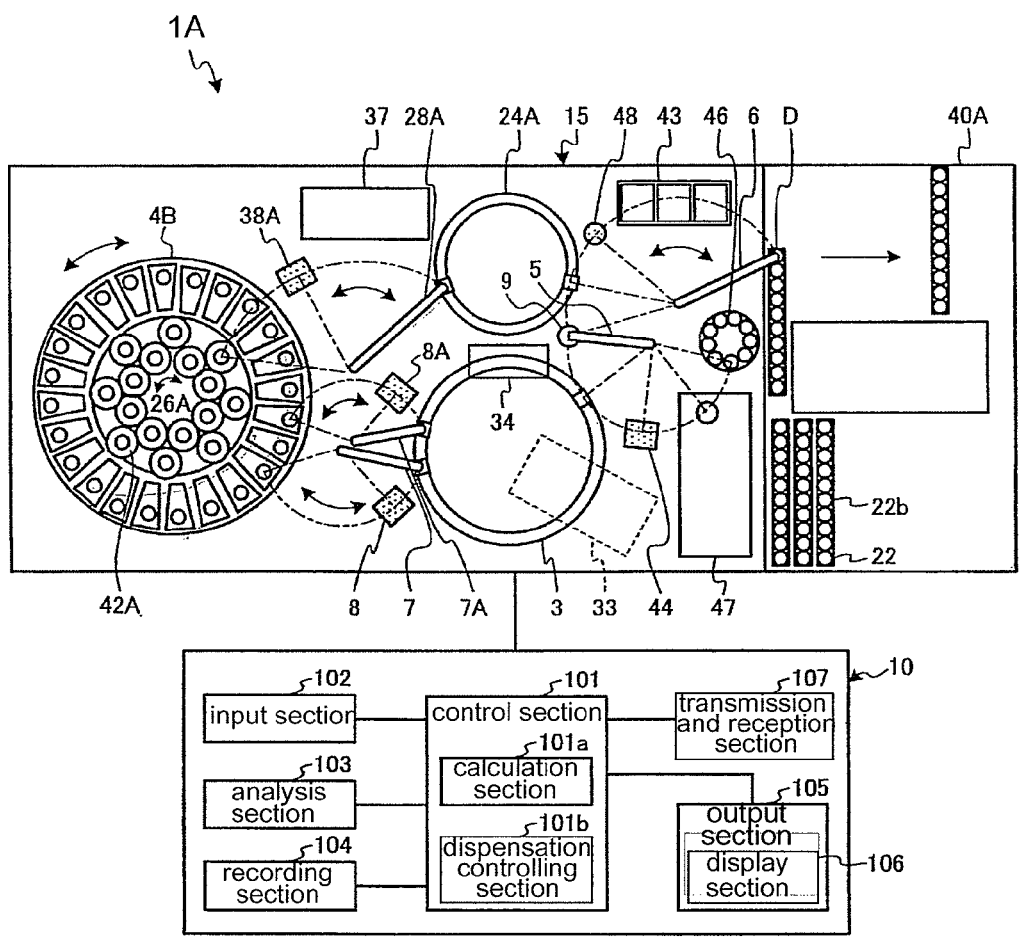
FIG. 9 is a schematic configuration diagram illustrating an automatic analyzer according to Embodiment 2.

FIG. 9 is a schematic configuration diagram illustrating an automatic analyzer 1A according to Embodiment 2. The automatic analyzer 1A according to Embodiment 2 broadly includes an analysis unit 15, a control mechanism 10, and a sample container transferring mechanism 40A. The analysis unit 15 includes a first sample dispensing apparatus 6, a second sample dispensing apparatus 5, an aliquot container 9, a reaction table 3 (biochemistry), a reagent table 4B, an immune reaction table 24A, a reagent table 26A, reagent dispensing apparatuses 7, 7A and 28A, dispensing probe washing apparatus 8, 8A, 38A and 44, a reaction container washing apparatus 34, a tip loading unit 43, an emergency sample table 46, an electrolyte measuring apparatus (ISE) 47, and a reaction container disposal opening 48.

Steps substantially the same as those of the automatic analyzer 1 according to Embodiment 1 are adopted as the analysis steps for biochemical analysis and immunological analysis of the automatic analyzer 1A, and functions of constituents in a biochemical analysis module and an immunological analysis module are integrated in order to aggregate the biochemical analysis module and the immunological analysis module in one unit. Besides performing an immune reaction, the immune reaction table 24A also functions as an enzyme reaction table for performing an enzymatic reaction. The reagent table 4B and the reagent table 26A have a concentric circular structure, and the reagent table 4B is arranged outside and the reagent table 26A is arranged inside. The reagent table 4B and the reagent table 26A each include a driving section (not shown), so that they can independently rotate in the direction indicated by the arrow in FIG. 9. A reagent container 42A in the reagent table 26A has a cylindrical structure. Adjacent reagent containers 42A, are connected with one another with gears (not shown), driven by a driving section (not shown) to rotate as well as revolve over the reagent table 26A.

The emergency sample table 46 contains, not only an emergency sample, a retest sample and an interrupting sample, but also various other samples (such as a standard sample for creating a calibration curve, and an accuracy control sample) other than general samples. The electrolyte measuring apparatus (ISE) 47 is an apparatus for measuring electrolyte concentration (ion concentration) using an ion selective electrode. The reaction container disposal opening 48 is a disposal opening for the disposable reaction container 32A used for immunological analysis.

Such an integrated apparatus, which includes a biochemical analysis module and an immunological analysis module in one unit, as the automatic analyzer 1A, includes the first sample dispensing apparatus 6 which uses the disposable tip 60a, the second sample dispensing apparatus 5 which uses a reusable metal probe, and the aliquot container 9 for subdividing a sample for biochemical analysis. As a result, it becomes possible to avoid carry-over in a retest for immunological assay menu with a high carry-over avoiding level, and sample dispensing for biochemical assay menu with a low carry-over avoiding level and subsequent analysis do not need to be postponed, making it possible to significantly increase processing capability.

INDUSTRIAL APPLICABILITY

As described above, the automatic analyzer and sample dispensing method according to the present invention are useful for an automatic analyzer for optically measuring a reactant of a sample and a reagent to analyze components of the sample, and in particular, for an automatic analyzer for performing analysis of both assay menu with a high carry-over avoiding level and assay menu with a low carry-over avoiding level.

The invention claimed is:

1. An analyzer for performing an immunological assay and a biochemical assay of a sample from a sample container, the analyzer comprising:
an immunoassay unit configured to conduct an immunoassay in an immunoassay reaction vessel;
a biochemical assay unit configured to conduct a biochemical assay in a biochemical reaction vessel;
a first pipettor;
a second pipettor; and
a controller configured to direct the first pipettor to transfer a first amount of sample from a first sample container to a first aliquot container, to direct the first pipettor to transfer a second amount of sample from the first sample container to a first immunoassay reaction vessel, to direct the second pipettor to transfer a third amount of sample from the first aliquot container to a first biochemical reaction vessel, to direct the immunoassay unit to conduct a first immunoassay of the second amount of sample in the first immunoassay reaction vessel, and to direct the biochemical unit to conduct a first biochemical assay of the third amount of sample in the first biochemical reaction vessel.

2. The analyzer of claim 1 wherein the controller is further configured to direct the second pipettor to transfer a fourth amount of sample from the first aliquot container to a second biochemical reaction vessel and to direct the biochemical unit to conduct a second biochemical assay of the fourth amount of sample in the second biochemical reaction vessel.

3. The analyzer of claim 2 wherein the controller is further configured to calculate the minimum amount of sample required by the biochemical assay unit and to direct the first pipettor to transfer at least the minimum amount from the sample container to the first aliquot container, wherein the minimum amount is at least equal to the sum of the third amount of sample and the fourth amount of sample.

4. The analyzer of claim 1 further comprising a transport configured to move the first aliquot container from the first pipettor to the second pipettor, wherein the controller is configured to direct the transport to align the first aliquot container with the first pipettor during the transfer of the first amount of sample and to align the first aliquot container with the second pipettor during the transfer of the third amount of sample.

5. The analyzer of claim 1 wherein the controller is configured to direct the first pipettor to transfer the second amount of sample in parallel with the transfer of the third amount of sample by the second pipettor.

6. The analyzer of claim 1 wherein the first pipettor is configured to transfer the first amount of sample and the second amount of sample using a first disposable pipette tip and wherein the second pipettor is configured to transfer the third amount of sample using a reusable probe.

7. The analyzer of claim 6, wherein the controller is further configured to direct the first pipettor to transfer a fifth amount of sample from a second sample container to a second immunoassay reaction vessel using a second disposable pipette tip and to direct the first pipettor to transfer a sixth amount of sample from the first sample container to a second aliquot container using a third disposable pipette tip.

8. The analyzer of claim 7, wherein the first aliquot container and second aliquot container are the same container.

9. The analyzer of claim 1 wherein the first pipettor includes a first arm and the second pipettor includes a second arm, and wherein the first arm and the second arm are supported on a common pivoting axis.

10. The analyzer of claim 1 wherein the immunoassay unit includes a rotatable immunoassay reagent table and a rotatable immunoassay reaction table, the immunoassay reaction table configured to support the first immunoassay reaction vessel, the immunoassay reaction table configured to align the first immunoassay reaction vessel to the first pipettor during the transfer of the second amount of sample.

11. An analyzer for performing an immunological assay and a biochemical assay of a sample from a sample container, the analyzer having a retest determination capability, the analyzer comprising:
an immunoassay unit configured to conduct an immunoassay in an immunoassay reaction vessel;
a biochemical assay unit configured to conduct a biochemical assay in a biochemical reaction vessel;
a first pipettor;
a second pipettor; and
a controller configured to direct the first pipettor to transfer a first sample amount from a sample container to an aliquot container, to direct the second pipettor to transfer a second amount of sample from the aliquot container to a first biochemical reaction vessel, to direct the biochemical unit to conduct a first biochemical assay of the second amount of sample in the first biochemical reaction vessel,
wherein, when the analyzer determines that a retest biochemical assay is necessary, the controller directs the first pipettor to transfer a third amount of sample from the sample container to the aliquot container, to direct the second pipettor to transfer a fourth amount of sample from the aliquot container to a second biochemical reaction vessel, and to direct the biochemical unit to conduct a second biochemical assay of the fourth amount of sample in the second biochemical reaction vessel.

12. The analyzer of claim 11, wherein the controller directs the first pipettor to transfer a fifth amount of sample from the sample container to an immunoassay reaction vessel, and wherein the transfer of the second amount of sample and the transfer of the fifth amount of sample occur in parallel.

13. The analyzer of claim 12, wherein the first pipettor is configured to transfer fluids using disposable pipette tips, and wherein the second pipettor is configured to transfer fluids using a reusable probe.

14. An analyzer for performing assays selected from two assay menus, the analyzer comprising:
a first assay unit configured to conduct an assay from a first assay menu;
a second assay unit configured to conduct an assay from a second assay menu;
a first pipettor;
a second pipettor;
a transport configured to move an aliquot container from the first pipettor to the second pipettor; and
a controller configured to calculate the minimum amount of sample required by the second assay unit, to direct the first pipettor to subdivide a sample by transferring at least the minimum amount of the sample from a sample container to an aliquot container, to direct the transport to move the aliquot container from the first pipettor to the second pipettor, to direct the first assay unit to conduct an assay from the first assay menu using a sample directly transferred from the sample container, and to direct the second assay unit to conduct an assay from the second assay menu using a sample transferred from the aliquot container.

15. The analyzer of claim 14, wherein the first assay unit is configured to conduct one or more of an immunoassay or a genetic assay.

16. The analyzer of claim 15, wherein the controller is further configured to determine whether a retest assay from the second assay unit is necessary, and
wherein, when the controller determines that a retest assay from the second assay unit is necessary, the controller directs the first pipettor to further subdivide the sample by transferring a second amount of the sample from the sample container to a second aliquot container.

17. The analyzer of claim 16, wherein the second assay unit is configured to conduct a biochemical assay.

18. The analyzer of claim 16 wherein the transport includes a rotating table and wherein the first aliquot container and the second aliquot container are disposed on the rotating table.

19. The analyzer of claim 16, wherein the first aliquot container and second aliquot container are the same container.

* * * * *